United States Patent
Bartsch et al.

(10) Patent No.: US 7,521,575 B2
(45) Date of Patent: Apr. 21, 2009

(54) STERICALLY HINDERED CHELATE PHOSPHINITE-PHOSPHITE LIGAND, CATALYST, COMPRISING AT LEAST ONE NICKEL(0) COMPLEX STABILIZED BY SAID LIGAND AND METHOD FOR PRODUCTION OF NITRILES

(75) Inventors: Michael Bartsch, Neustadt (DE);
Robert Baumann, Mannheim (DE);
Gerd Haderlein, Grünstadt (DE);
Miquel Angel Flores, Aranjuez (ES);
Tim Jungkamp, Kapellen (BE);
Hermann Luyken, Ludwigshafen (DE);
Jens Scheidel, Hirschberg (DE);
Wolfgang Siegel, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 277 days.

(21) Appl. No.: 10/577,138

(22) PCT Filed: Oct. 28, 2004

(86) PCT No.: PCT/EP2004/012176

§ 371 (c)(1), (2), (4) Date: Apr. 25, 2006

(87) PCT Pub. No.: WO2005/042547

PCT Pub. Date: May 12, 2005

(65) Prior Publication Data

US 2007/0060766 A1    Mar. 15, 2007

(30) Foreign Application Priority Data

Oct. 30, 2003 (DE) ................. 103 50 999

(51) Int. Cl.
C07C 253/00 (2006.01)
(52) U.S. Cl. .................................... 558/332
(58) Field of Classification Search ............. 558/332
See application file for complete search history.

(56) References Cited

U.S. PATENT DOCUMENTS

| | | | |
|---|---|---|---|
| 3,496,217 A | 2/1970 | Drinkard, Jr. et al. | |
| 3,496,218 A | 2/1970 | Drinkard, Jr. | |
| 3,766,237 A | 10/1973 | Chia et al. | |
| 3,850,973 A | 11/1974 | Seidel | |
| 3,903,120 A | 9/1975 | Shook, Jr. et al. | |
| 4,493,906 A | 1/1985 | Couvillion | |
| 4,587,369 A | 5/1986 | Cosyns et al. | |
| 4,704,492 A | 11/1987 | Nemet-Mavrodin | |
| 4,774,353 A | 9/1988 | Hall et al. | |
| 4,874,884 A | 10/1989 | McKinney et al. | |
| 5,523,453 A | 6/1996 | Breikss | |
| 5,693,843 A | 12/1997 | Breikss et al. | |
| 5,981,772 A | 11/1999 | Foo et al. | |
| 6,127,567 A | 10/2000 | Garner et al. | |
| 6,171,996 B1 | 1/2001 | Garner et al. | |
| 2003/0144440 A1* | 7/2003 | Gagne et al. | 526/274 |

FOREIGN PATENT DOCUMENTS

| | | |
|---|---|---|
| DE | 2237703 | 2/1973 |
| DE | 10136488 | 2/2003 |
| WO | WO-99/13983 | 3/1999 |
| WO | WO-99/64155 | 12/1999 |
| WO | WO-03/045552 | 6/2003 |
| WO | WO-03/062171 | 7/2003 |

OTHER PUBLICATIONS

Iovu et al., 1975, CAS: 84: 89741.*
H. Schindlbauer, 1965. Monatshefte Chemie, vol. 96, pp. 1936-1942.
Ullmanns Enzyklopadie der technischen Chemie, vol. 1, 3rd Ed., 1951, p. 769-776.
Ullmanns Enzyklopadie der technischen Chemie, vol. 1, 3rd Ed., 1951, pp. 743-755.
International Search Report No. PCT/EP2004/012176, dated Mar. 10, 2005, 2 pages.
"Applied Homogeneous Catalysis with Organometalic Compounds", vol. 1, VCH Weinhelm, p. 10 and 479-481.

* cited by examiner

Primary Examiner—Rei-tsang Shiao
(74) Attorney, Agent, or Firm—Connolly Bove Lodge & Hutz LLP

(57) ABSTRACT

The invention relates to phosphinite phosphites I of formula 1, 2, 3, 4, 5 or 6 and mixtures thereof, wherein R1, R2, R4 independently represent an alkyl or alkylene group with 1 to 8 carbon atoms, provided that at least one of the groups R1, R2, R4 is different from H; R5 to R22 independently represent H, an alkyl or alkylene group with 1 to 8 carbon atoms; R3 is H, methyl or ethyl; X is F, Cl or $CF_3$, if n=1 or 2 and X is H, if n=0.

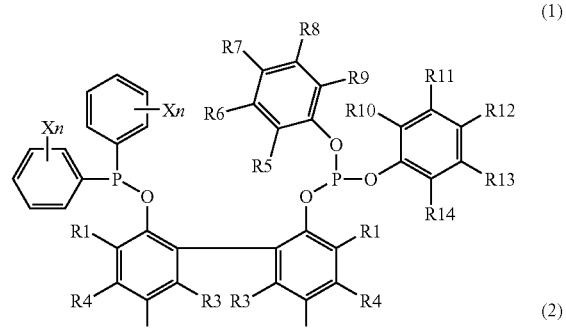

(1)

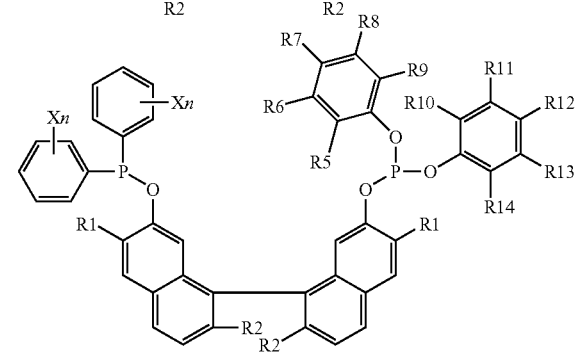

(2)

-continued
(3)
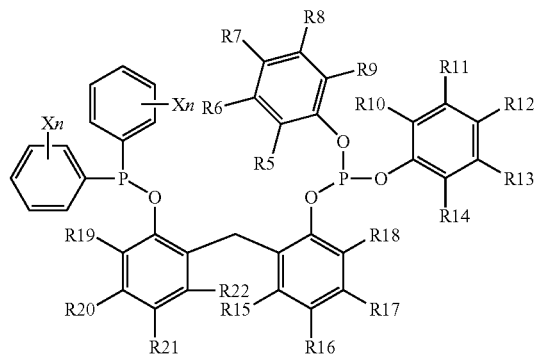
(4)
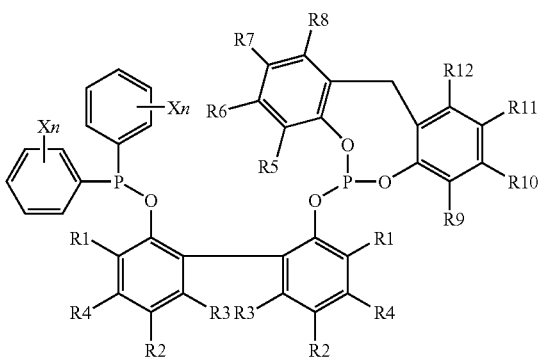
-continued
(5)
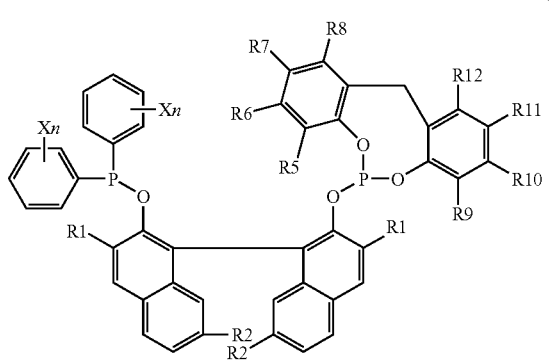
(6)
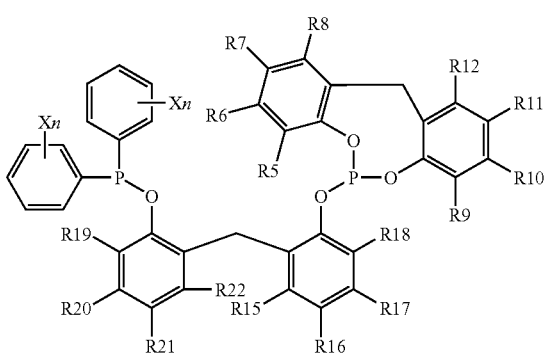
15 Claims, No Drawings

STERICALLY HINDERED CHELATE PHOSPHINITE-PHOSPHITE LIGAND, CATALYST, COMPRISING AT LEAST ONE NICKEL(0) COMPLEX STABILIZED BY SAID LIGAND AND METHOD FOR PRODUCTION OF NITRILES

CROSS REFERENCE TO RELATED APPLICATION

The present application is a National Stage application of PCT/EP2004/012176, filed Oct. 28, 2004, which claims priority from German Pat. Appl. No. 10350999.2, filed Oct. 30, 2003.

The present invention relates to novel phosphinite phosphites, in particular chelate phosphinite phosphites, and to a process for their preparation. The present invention further provides their use as a ligand in transition metal complexes, novel transition metal complexes and appropriate processes for their preparation. Moreover, the present invention relates to the use of the transition metal complexes as a catalyst and to processes in the presence of such transition metal complexes as a catalyst.

Chelate phosphinite phosphites, nickel complexes having such phosphinite phosphite ligands and the use of such complexes as a catalyst are known.

U.S. Pat. No. 5,693,843 and 5,523,453 describe processes for hydrocyanating unsaturated organic compounds and the isomerization of nitriles in the presence of nickel(0) complexes having chelate phosphinite phosphites as a ligand. It is desirable to improve the stability of the chelate phosphinite phosphite ligands to increase the on-stream time of the catalyst. Also desirable are an improvement in the selectivity of the catalyst, for example for 3-pentenenitrile in the hydrocyanation of butadiene or for adiponitrile in the hydrocyanation of 3-pentenenitrile, and an improvement in the space-time yield.

It is an object of the present invention to provide phosphinite phosphites which are suitable as chelate phosphinite phosphites and enable, in a technically simple and economic manner, the hydrocyanation of unsaturated organic compounds with high stability, high reactivity and high selectivity of the catalyst.

We have found that this object is achieved by phosphinite phosphites I of the formula 1 or 2 or 3 or 4 or 5 or 6

Formula 1

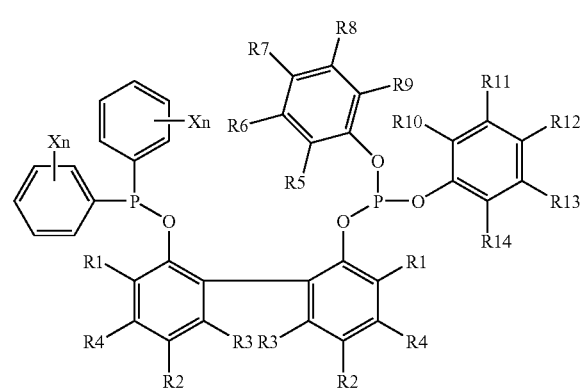

Formula 2

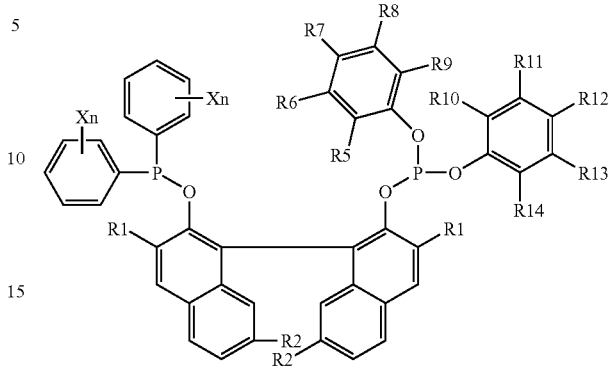

Formula 3

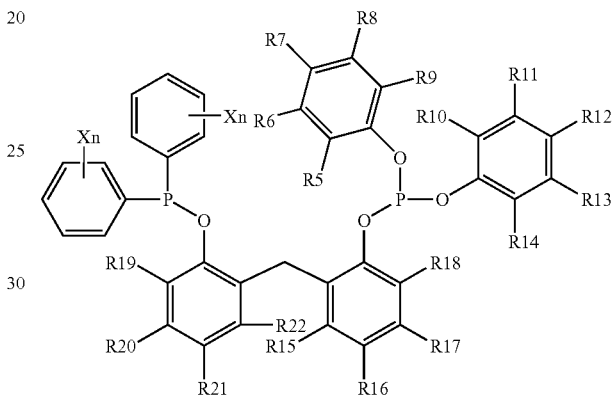

Formula 4

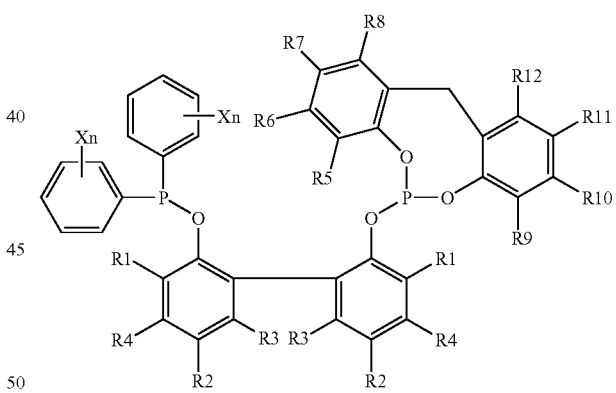

Formula 5

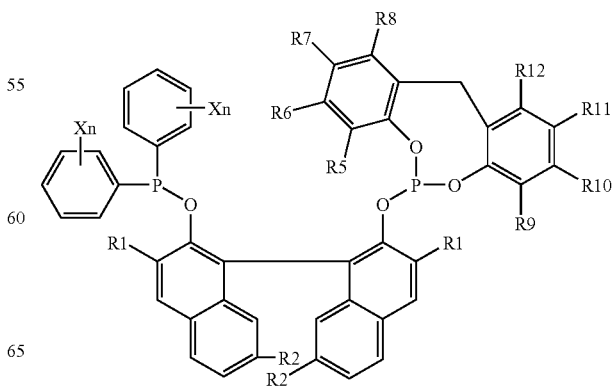

-continued

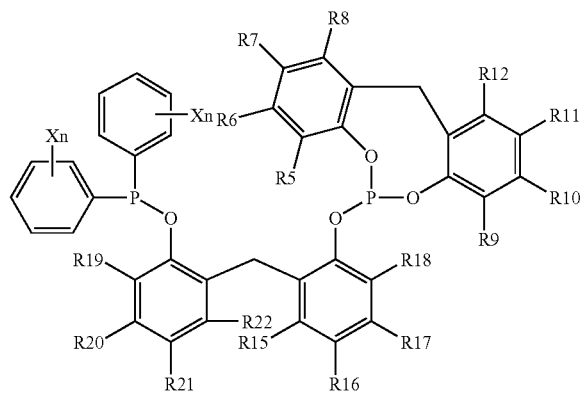

Formula 6 where

R1, R2, R4 are each independently an alkyl or alkylene group having from 1 to 8 carbon atoms, with the proviso that at least one of the R1, R2, R4 groups is not H, R5 to R22 are each independently H, an alkyl or alkylene group having from 1 to 8 carbon atoms, R3 is H, methyl or ethyl, X is F, Cl or $CF_3$ when n is 1 or 2, X is H, when n is 0, and their mixtures.

According to the invention, the R1, R2, R4 radicals are each independently an alkyl or alkylene group having from 1 to 8 carbon atoms, with the proviso that at least one of the R1, R2, R4 groups is not H.

When R1 is hydrogen, R2 may be hydrogen and R4 an alkyl or alkylene group having from 1 to 8 carbon atoms, or R2 may be an alkyl or alkylene group having from 1 to 8 carbon atoms and R4 hydrogen, or R2 and R4 may each independently be an alkyl or alkylene group having from 1 to 8 carbon atoms.

When R1 is an alkyl or alkylene group having from 1 to 8 carbon atoms, R2 and R4 may each be hydrogen, or R2, independently of R1, may be an alkyl or alkylene group having from 1 to 8 carbon atoms and R4 hydrogen, or R2 may be hydrogen and R4, independently of R1, an alkyl or alkylene group having from 1 to 8 carbon atoms, or R2 and R4 may each independently and independently of R1 be an alkyl or alkylene group having from 1 to 8 carbon atoms.

An alkyl or alkylene group having from 1 to 8 carbon atoms is preferably an alkyl group having from 1 to 8 carbon atoms, in particular from 1 to 4 carbon atoms, advantageously selected from the group consisting of methyl, ethyl, n-propyl, isopropyl, n-butyl, s-butyl, isobutyl and t-butyl, in particular from the group consisting of methyl, ethyl, n-propyl, isopropyl and t-butyl.

According to the invention, R3 is H or a methyl or ethyl group. According to the invention, the phenyl groups joined to a phosphorus atom may be unsubstituted or each independently bear 1 or 2 substituents X per phenyl group, so that n may have the value 0, 1 or 2.

The two phenyl groups joined to a phosphorus atom may be substituted identically or differently, and, in the case of different substitution, the differences relate both to the number of substituents and to the type of substituents. In the context of the present invention, the formulae 1, 2 and 3 include both identical and different substitution of the phenyl groups joined to a phosphorus atom.

According to the invention, X is F, Cl or $CF_3$, preferably F or $CF_3$. In the case that n is 2, the two X1 and X2 radicals may each independently be F, Cl or $CF_3$, i.e. F and F, F and Cl, F and $CF_3$, Cl and Cl, Cl and $CF_3$, $CF_3$ and $CF_3$, preferably F and F, $CF_3$ and $CF_3$.

In a preferred embodiment, in the case that n is 1 and X is F, a useful substitution is in the m-position to the phosphorus atom joined to the phenyl ring in a phenyl ring joined to a phosphorus atom.

In a further preferred embodiment, in the case that n is 1 and X is $CF_3$, a useful substitution is in the p-position to the phosphorus atom joined to the phenyl ring in a phenyl ring joined to a phosphorus atom.

In a preferred embodiment, in the case that n is 2 and X1 and X2 are each F, a useful substitution is in the two m-positions to the phosphorus atom joined to the phenyl ring in a phenyl ring joined to a phosphorus atom.

In a further preferred embodiment, in the case that n is 2 and X1 and X2 are each $CF_3$, a useful substitution is in the two m-positions to the phosphorus atom joined to the phenyl ring in a phenyl ring joined to a phosphorus atom.

Particularly preferred phosphinite phosphites are those of the following formulae 1a-1j with the R1, R2, R3 and R4, and also R18 to R22, groups each as defined in Table 1.

Formula Ia

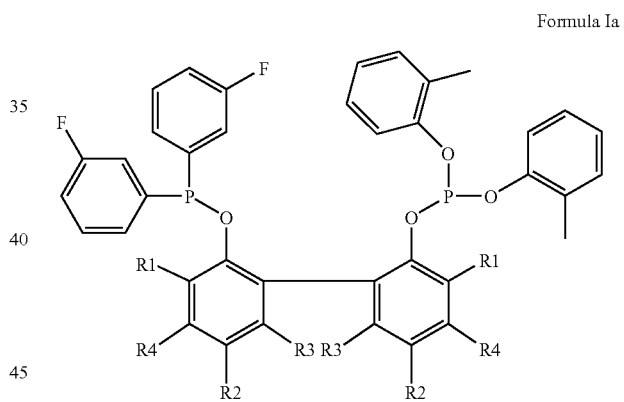

Formula Ib

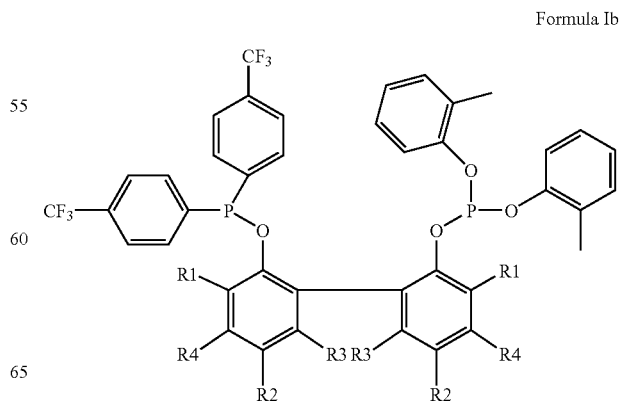

Formula Ic
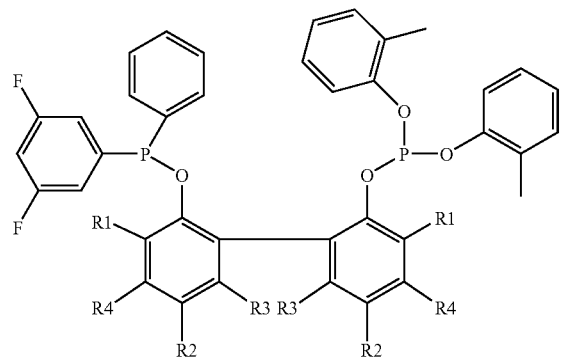
Formula Id
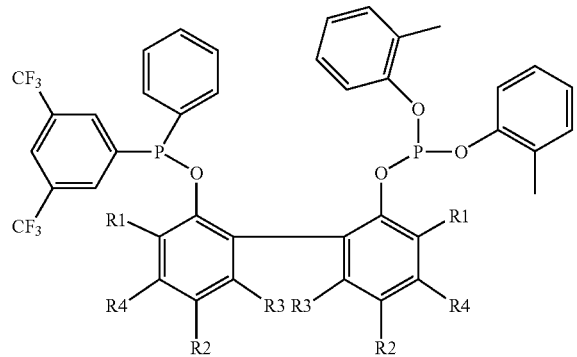
Formula Ie
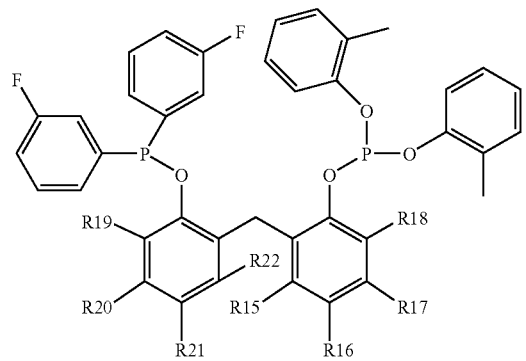
Formula If
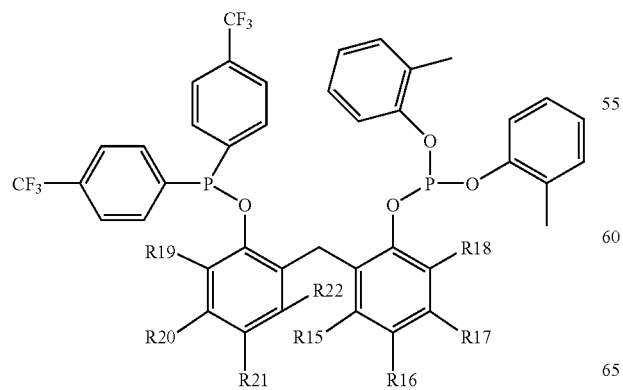
Formula Ig
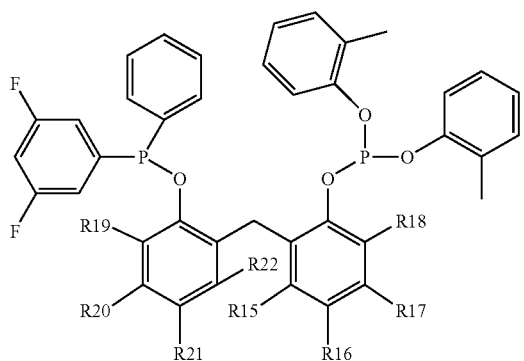
Formula Ih
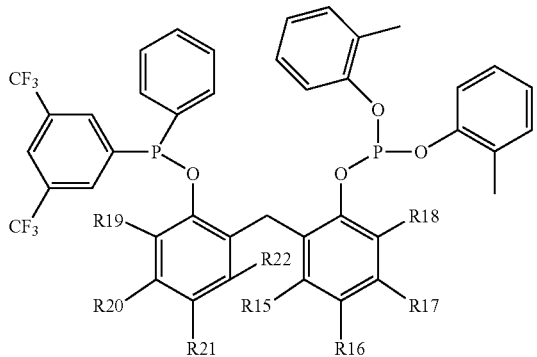
Formula Ii
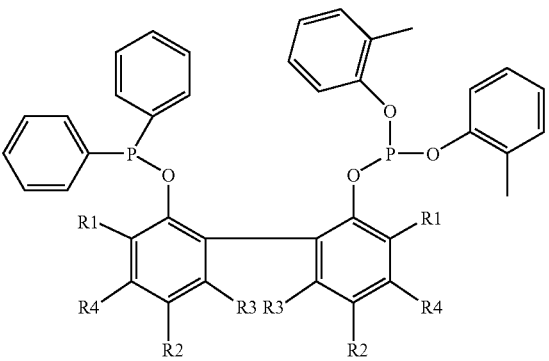
Formula Ij
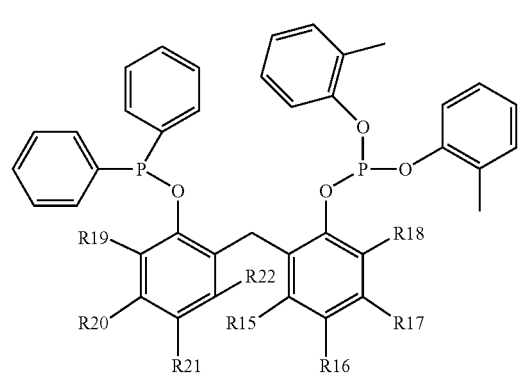

In these formulae, the R1, R2, R3 and R4, and also R18 to R22, radicals are each defined as follows:

TABLE 1

| Formula | R1, R18, R19 | R2, R16, R21 | R3, R15, R22 | R4, R17, R20 |
|---|---|---|---|---|
| Ia1, Ib1, Ic1, Id1, Ie1, If1, Ig1, Ih1, Ii1, Ij1 | Me | Me | H | H |
| Ia2, Ib2, Ic2, Id2, Ie2, If2, Ig2, Ih2, Ii2, Ij2 | Et | t-Bu | H | H |
| Ia3, Ib3, Ic3, Id3, Ie3, If3, Ig3, Ih3, Ii3, Ij3 | i-Pr | H | Me | H |
| Ia4, Ib4, Ic4, Id4, Ie4, If4, Ig4, Ih4, Ii4, Ij4 | t-Bu | t-Bu | H | H |
| Ia5, Ib5, Ic5, Id5, Ie5, If5, Ig5, Ih5, Ii5, Ij5 | Et | Me | H | H |
| Ia6, Ib6, Ic6, Id6, Ie6, If6, Ig6, Ih6, Ii6, Ij6 | n-Pr | Me | H | H |
| Ia7, Ib7, Ic7, Id7, Ie7, If7, Ig7, Ih7, Ii7, Ij7 | t-Bu | Me | H | H |
| Ia8, Ib8, Ic8, Id8, Ie8, If8, Ig8, Ih8, Ii8, Ij8 | Me | H | Me | Me |
| Ia9, Ib9, Ic9, Id9, Ie9, If9, Ig9, Ih9, Ii9, Ij9 | Me | t-Bu | H | H |

Further particularly preferred phosphinite phosphites are those of the following formulae Ik-Io.

Formula Ik

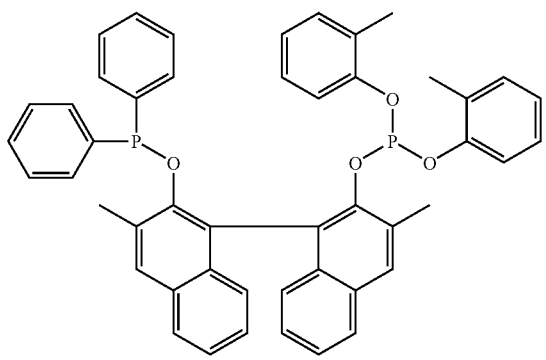

Formula Il

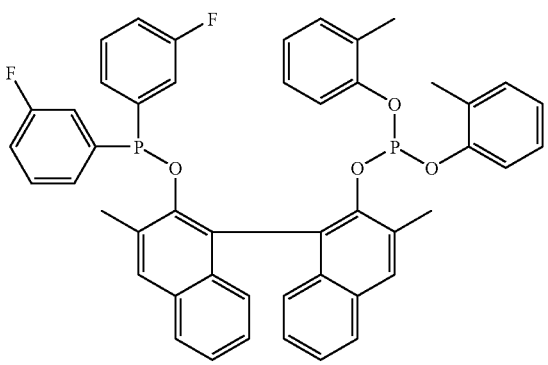

Formula Im

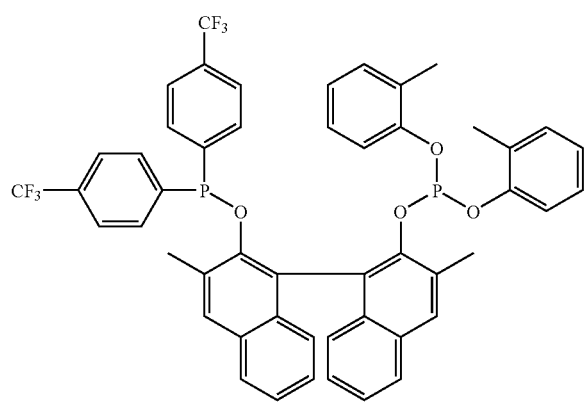

Formula In

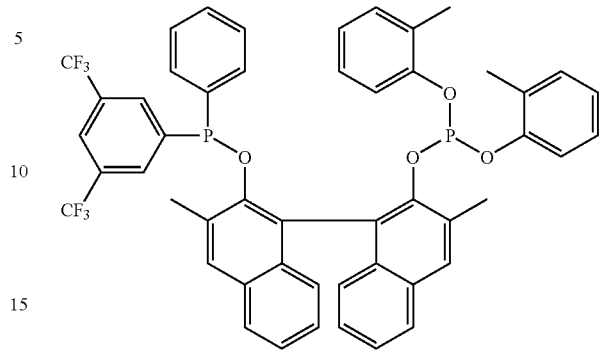

Formula Io

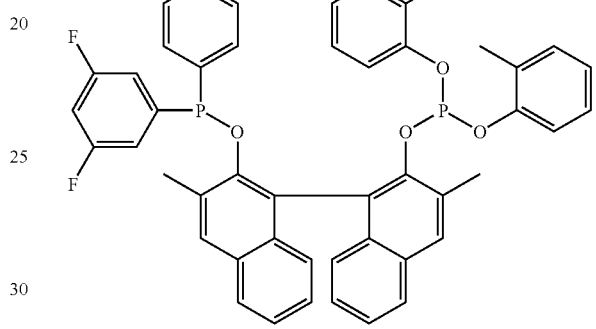

In Table 1, the abbreviations are each defined as follows:
H: hydrogen
Me: methyl
Et: ethyl
n-Pr: n-propyl
t-Bu: t-butyl To prepare phosphinite phosphite I, the procedure may be in accordance with the preparative processes, described in the U.S. Pat. Nos. 5,523,453 and 5,693,843, and also in WO 03/62171, for the phosphorus chelate ligands described there, for example by reaction of an optionally substituted (Xn-phenyl)(Xn-phenyl)phosphine chloride with a diol bearing the R1, R2, R3 and R4, and also R15 to R22 groups, and subsequent reaction with a (Rn-phenoxy)(Rn-phenoxy)phosphine chloride.

The preparation succeeds efficiently and economically from readily available reactants.

The diphenylphosphine chlorides used as a starting compound and their preparation are known per se, for example from: H. Schindlbauer, Monatshefte Chemie, Volume 96, 1965, pages 1936-1942. The process described there for preparing 4-fluorophenyldichlorophosphine may be employed in a similar manner to prepare the (Xn-phenyl)(Xn-phenyl) phosphine chlorides. The optimum parameters for preparing the particular (Xn-phenyl)(Xn-phenyl)phosphine chlorides may be determined readily by a few simple preliminary experiments.

The phosphinite phosphites I may be used as ligands in transition metal complexes.

Advantageous transition metals in this context are the metals of transition groups 1 to 2 and 6 to 8 of the periodic table, preferably of transition group 8 of the periodic table, more preferably iron, cobalt and nickel, in particular nickel.

When nickel is used, it may be present in different valencies, such as 0, +1, +2, +3. Preference is given in this context to nickel(0) and nickel(+2), in particular nickel(0).

To prepare the transition metal complexes, a transition metal-containing chemical compound or preferably a transition metal may be reacted with a phosphinite phosphite I, and the phosphinite phosphite I used may be an individual phosphinite phosphite I or a mixture of a plurality of phosphinite phosphites I.

The transition metal may be obtained before the reaction from suitable chemical compounds, for example from salts such as chlorides by reducing with base metals such as zinc.

When a compound containing one transition metal is used to prepare the transition metal complexes, advantageous compounds for this purpose are salts such as chlorides, bromides, acetylacetonates, sulfates, nitrates, for example nickel (II) chloride, or Ni(0) complexes such as bis(1,5-cyclooctadiene)Ni(0).

After the reaction of the compound containing one transition metal or of the transition metal with a phosphinite phosphite I, the valency of the transition metal in the complex may be changed using suitable oxidizing or reducing agents, for example non-noble metals such as zinc, or hydrogen in chemically bonded form such as sodium borohydride, or in molecular form, or electrochemically.

In a particularly preferred embodiment, a useful reaction is of a complex of Ni(0) having organic monophosphine, monophosphinite, monophosphonite or monophosphite ligands with a phosphinite phosphite I in accordance with the process described in the German patent application 10136488.1.

In the transition metal complexes, the molar ratio of transition metal to phosphinite phosphite I may be in the range from 1 to 6, preferably from 2 to 5, in particular 2, 3 or 4.

The transition metal complexes may be free of ligands other than the phosphinite phosphites I.

In addition to the phosphinite phosphites I, the transition metal complexes may contain further ligands, for example nitriles such as acetonitrile, adiponitrile, 3-pentenenitrile, 4-pentenenitrile, 2-methyl-3-butenenitrile, olefins such as butadiene, or phosphorus compounds such as organic monophosphines, monophosphinites, monophosphonites or monophosphites.

The preparation of such transition metal complexes may in principle be effected in such a way as described in the literature, for example in DE-A-2 237 703, U.S. Pat. No. 3,850,973, U.S. Pat. No. 3,766,237 or U.S. Pat. No. 3,903,120, to prepare transition metal complexes which contain tri-o-tolyl phosphite, tri-m-tolyl phosphite or tri-p-tolyl phosphite, by partly or fully replacing these phosphites with the inventive phosphinite phosphites I.

The inventive transition metal complexes may be used as a catalyst, in particular as a homogeneous catalyst.

It has been found to be particularly advantageous to use the inventive transition metal complexes as a catalyst in the addition of hydrocyanic acid to olefinic double bonds, in particular those which are conjugated to a further olefinic double bond, for example butadiene to obtain a mixture comprising 2-methyl-3-butenenitrile and 3-pentenenitrile. Equally advantageous is the use as a catalyst in the addition of hydrocyanic acid to olefinic double bonds which are not associated with a further olefinic double bond, for example 3-pentenenitrile or 4-pentenenitrile or mixtures thereof, preferably 3-pentenenitrile, to obtain adiponitrile, or 3-pentenoic ester or 4-pentenoic ester or mixtures thereof, preferably 3-pentenoic ester, to obtain 5-cyanovaleric ester.

It has likewise been found to be particularly advantageous to use the inventive transition metal complexes as a catalyst in the isomerization of organic nitriles, especially those in which the nitrile group is not conjugated to an olefinic double bond, for example 2-methyl-3-butenenitrile to obtain 3-pentenenitrile. Equally advantageous is also the use as a catalyst in the isomerization of organic nitriles in which the nitrile group is conjugated to an olefinic double bond.

Processes for adding hydrocyanic acid to an olefinic double bond or for isomerizing organic nitriles may in principle be effected in such a way as described, for example, in WO 99/13983 or WO 99/64155 by partly or fully replacing the phosphonites described there with the inventive phosphinite phosphites I.

The invention further provides a process for preparing mixtures of monoolefinic $C_5$-mononitriles having nonconjugated C=C and C≡N bonds by hydrocyanating a 1,3-butadiene-containing hydrocarbon mixture in the presence of a catalyst, wherein the hydrocyanation is effected in the presence of at least one of the above-described inventive systems.

To prepare monoolefinic $C_5$-mononitriles by the process according to the invention, preference is given to using a hydrocarbon mixture which has a 1,3-butadiene content of at least 10% by volume, preferably at least 25% by volume, in particular at least 40% by volume.

To prepare mixtures of monoolefinic $C_5$-mononitriles which comprise, for example, 3-pentenenitrile and 2-methyl-3-butenenitrile and are suitable as intermediates for further processing to adiponitrile, pure butadiene or 1,3-butadiene-containing hydrocarbon mixtures may be used.

1,3-Butadienic hydrocarbon mixtures are obtainable on the industrial scale. For example, in the workup of mineral oil by steam-cracking naphtha, a hydrocarbon mixture referred to as a $C_4$ cut and having a high total olefin fraction, about 40% being accounted for by 1,3-butadiene and the remainder by monoolefins and polyunsaturated hydrocarbons and also alkanes, is obtained. These streams always also contain small fractions of generally up to 5% of alkynes, 1,2-dienes and vinylacetylene.

Pure 1,3-butadiene may be isolated from industrially obtainable hydrocarbon mixtures, for example, by extractive distillation.

$C_4$ cuts are optionally substantially freed of alkynes, e.g. propyne or butyne, of 1,2-dienes, e.g. propadiene, and of alkenynes, e.g. vinylacetylene. Otherwise, under some circumstances, products are obtained in which a C=C double bond is conjugated with the C≡N bond. "Applied Homogeneous Catalysis with Organometalic Compounds", Vol. 1, VCH Weinheim, p. 479 discloses that conjugated 2-pentenenitrile which is formed in the isomerization of 2-methyl-3-butenenitrile and 3-pentenenitrile acts as a reaction inhibitor for the secondary addition of hydrogen cyanide to adiponitrile. It has been found that the abovementioned conjugated nitriles obtained in the hydrocyanation of an unpretreated $C_4$ cut also act as catalyst poisons for the first reaction step of adipic acid preparation, the monoaddition of hydrogen cyanide.

Therefore, those components which give rise to catalyst poisons in the course of catalytic hydrocyanation, especially alkynes, 1,2-dienes and mixtures thereof, are optionally partly or fully removed from the hydrocarbon mixture. To remove these components, the $C_4$ cut, before the addition of hydrogen cyanide, is preferably subjected to a catalytic partial hydrogenation. This partial hydrogenation is effected in the presence of a hydrogenation catalyst which is capable essentially of selectively hydrogenating alkynes and 1,2-dienes in addition to other dienes and monoolefins.

Suitable heterogeneous catalyst systems generally comprise a transition metal compound on an inert support. Suitable inorganic supports are the oxides which are customary for this purpose, in particular silicon oxides and aluminum oxides, aluminosilicates, zeolites, carbides, nitrides, etc., and mixtures thereof. The supports used are preferably $Al_2O_3$, $SiO_2$ and mixtures thereof. They are in particular the heterogeneous catalysts used in U.S. Pat. No. 4,587,369; U.S. Pat. No. 4,704,492 and U.S. Pat. No. 4,493,906 which are fully incorporated here by way of reference. Further suitable Cu-based catalyst systems are sold by Dow Chemical as KLP catalyst.

The addition of hydrogen cyanide to 1,3-butadiene or a 1,3-butadiene-containing hydrocarbon mixture, for example a pretreated, part-hydrogenated $C_4$ cut, may be effected continuously, semicontinuously or batchwise.

In a suitable variant of the process according to the invention, the addition of the hydrogen cyanide is effected continuously. Suitable reactors for the continuous reaction are known to those skilled in the art and are described, for example, in Ullmanns Enzyklopädie der technischen Chemie, Vol. 1, 3rd Ed., 1951, p. 743 ff. Preference is given to using a stirred tank battery or a tubular reactor for the continuous variant of the process according to the invention.

In a preferred variant of the process according to the invention, the addition of the hydrogen cyanide to 1,3-butadiene or a 1,3-butadiene-containing hydrocarbon mixture is effected semicontinuously.

The semicontinuous process comprises:
a) charging a reactor with the hydrocarbon mixture, optionally a portion of the hydrogen cyanide and an inventive hydrocyanation catalyst which may optionally have been generated in situ, and also optionally a solvent,
b) reacting the mixture at elevated temperature and elevated pressure by feeding in hydrogen cyanide in semicontinuous mode in accordance with its consumption,
c) completing the reaction by continued reaction and subsequent workup.

Suitable pressure-rated reactors are known to those skilled in the art and are described for example, in Ullmanns Enzyklopädie der technischen Chemie, Vol. 1, 3rd Edition, 1951, p. 769 ff. In general, an autoclave is used for the process according to the invention which, if desired, may be equipped with a stirrer apparatus and an internal lining. For the above steps, the following should preferably be taken into account:

Step a):

The pressure-rated reactor is charged before the start of the reaction with the part-hydrogenated $C_4$ cut or butadiene, hydrogen cyanide, a hydrocyanation catalyst and also optionally a solvent. Suitable solvents are the preferably aromatic hydrocarbons which have been mentioned above for the preparation of the inventive catalysts, such as toluene and xylene, or tetrahydrofuran.

Step b):

The conversion of the mixture is generally effected at elevated temperature and elevated pressure. The reaction temperature is generally in the range from about 0 to 200° C., preferably from about 50 to 150° C. The pressure is generally in the range from about 1 to 200 bar, preferably from about 1 to 100 bar, in particular from 1 to 50 bar, especially preferably from 1 to 20 bar. During the reaction hydrogen cyanide is fed in accordance with its consumption, in the course of which the pressure in the autoclave remains substantially constant. The reaction time is from about 30 minutes to 5 hours.

Step c):

To complete the conversion, the reaction time may be followed by a continued reaction time of from 0 minutes to about 5 hours, preferably from about 1 hour to 3.5 hours, in which no more hydrogen cyanide is fed into the autoclave. In this time, the temperature is left substantially constant at the reaction temperature set beforehand. The workup is effected by common methods and comprises the removal of the unconverted 1,3-butadiene and of the unconverted hydrogen cyanide, for example by washing or extracting, and the distillative workup of the remaining reaction mixture to remove the products of value and recover the still-active catalyst.

In a further suitable variant of the process according to the invention, the addition of hydrogen cyanide to the 1,3-butadiene-containing hydrocarbon mixture is effected batchwise. The reaction conditions described for semicontinuous processes are substantially retained, although no additional hydrogen cyanide is fed in in step b) and it is instead fully initially charged.

Generally, the preparation of adiponitrile from a butadiene-containing mixture by adding 2 molar equivalents of hydrogen cyanide can be divided into three steps:
1. Preparation of $C_5$ monoolefin mixtures having nitrile function.
2. isomerization of the 2-methyl-3-butenenitrile present in these mixtures to 3-pentenenitrile and isomerization of the 3-pentenenitrile formed in this way and already present in the mixtures from step 1 to different n-pentenenitriles. This should form a very high fraction of 3-pentenenitrile and/or 4-pentenenitrile and a very small fraction of conjugated 2-pentenenitrile and 2-methyl-2-butenenitrile which are in some cases active as catalyst poison.
3. Preparation of adiponitrile by adding hydrogen cyanide to the 3-pentenenitrile formed in step 2 which has been isomerized beforehand in situ to 4-pentenenitrile. The by-products which occur are, for example, 2-methylglutarodinitrile from the Markovnikov addition of hydrogen cyanide to 4-pentenenitrile or the anti-Markovnikov addition of hydrogen cyanide to 3-pentenenitrile and ethylsuccinonitrile from the Markovnikov addition of hydrogen cyanide to 3-pentenenitrile.

The inventive catalysts based on phosphinite ligands are also advantageously suitable for the positional and double bond isomerization in step 2 and/or the secondary addition of hydrogen cyanide in step 3.

Advantageously, the catalysts used in accordance with the invention do not only exhibit a high selectivity in relation to the monoaddition products obtained in the hydrocyanation of 1,3-butadiene-containing hydrocarbon mixtures, but they may also be admixed with an excess of hydrogen cyanide in the hydrocyanation without noticeable deposition of inactive nickel(II) compounds, for example nickel(II) cyanide. Unlike known hydrocyanation catalysts based on uncomplexed phosphine and phosphinite ligands, the catalysts containing a phosphinite phosphite I are thus suitable not only for continuous hydrocyanation processes in which a hydrogen cyanide excess is generally effectively avoided in the reaction mixture, but also for semicontinuous and batch processes in which there is generally a high hydrogen cyanide excess. The catalysts used in accordance with the invention and the processes for the hydrocyanation based on them thus generally have higher catalyst recycle rates and longer catalyst on-stream times than existing processes. In addition to better economic viability, this is also advantageous from the ecological viewpoint since the nickel cyanide formed from the active catalyst with hydrogen cyanide is highly poisonous and has to be worked up or disposed of at high cost.

In addition to the hydrocyanation of 1,3-butadiene-containing hydrocarbon mixtures, the inventive systems are generally suitable for all common hydrocyanation processes.

These include in particular the hydrocyanation of nonactivated olefins, for example of styrene and 3-pentenenitrile.

The addition of hydrocyanic acid to an olefinic double bond in the presence of an inventive catalyst system, especially the addition to butadiene, a butadiene or to 3-pentenenitrile, 4-pentenenitrile or mixtures of such pentenenitriles, or the isomerization of organic nitriles in the presence of an inventive catalyst system, especially the isomerization of 2-methyl-3-butenenitrile to 3-pentenenitrile, may advantageously be carried out in the presence of one or more Lewis acids as promoters which influence the activity, selectivity or both of the inventive catalyst system. Useful promoters are inorganic and organic compounds in which the cation is selected from the group consisting of scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_4$, $TiCl_3$, $ClTi(O\text{-}iso\text{-}Pr)_3$, $MnCl_2$, $ScCl_3$, $AlCl_3$, $(C_2H_5)AlCl_2$, $(C_2H_5)_2AlCl$, $(C_2H_5)_3Al_2Cl_3$, $(C_8H_{17})AlCl_2$, $(C_8H_{17})_2AlCl$, $(iso\text{-}C_4H_9)_2AlCl$, $Ph_2AlCl$, $PhAlCl_2$, $ReCl_5$, $ZrCl_4$, $ZrCl_2$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$, as generally described in U.S. Pat. No. 6,171,996 B1. Preferred promoters are also described in U.S. Pat. No. 3,496,217, U.S. Pat. No. 3,496,218 and U.S. Pat. No. 4,774,353. These include metal salts such as $ZnCl_2$, $CoI_2$ and $SnCl_2$, and organometallic compounds such as $RAlCl_2$, $R_3SnO_3SCF_3$, and $R_3B$, where R is an alkyl group or aryl group. U.S. Pat. No. 4,874,884 describes how synergistically active combinations of promoters, may be selected in order to increase the catalytic activity of the catalyst system. Preferred promoters include $CdCl_2$, $FeCl_2$, $ZnCl_2$, $B(C_6H_5)_3$ and $(C_6H_5)_3SnZ$ where Z is $CF_3SO_3$, $CH_3C_6H_4SO_3$ or $(C_6H_5)_3BCN$.

The molar ratio of promoter to nickel in the catalyst system may be between 1:16 and 50:1.

A further advantageous embodiment of the hydrocyanation and isomerization can be taken from U.S. Pat. No. 5,981,772, whose contents are fully incorporated in the present application by reference, with the proviso that an inventive system or a mixture of such systems is used instead of the catalysts specified in this patent specification.

A further advantageous embodiment of the hydrocyanation and isomerization can be taken from U.S. Pat. No. 6,127,567, whose contents are fully incorporated in the present application by reference, with the proviso that an inventive system or a mixture of such systems is used instead of the catalysts specified in this patent specification.

A further advantageous embodiment of the hydrocyanation can be taken from U.S. Pat. No. 5,693,843, whose contents are fully incorporated in the present application by reference, with the proviso that an inventive system or a mixture of such systems is used instead of the catalysts specified in this patent specification.

A further advantageous embodiment of the hydrocyanation can be taken from U.S. Pat. No. 5,523,453, whose contents are fully incorporated in the present application by reference, with the proviso that an inventive system or a mixture of such systems is used instead of the catalysts specified in this patent specification.

The invention is illustrated in detail with reference to the nonlimiting examples which follow.

EXAMPLES

The yields were determined by gas chromatography (column: 30 m HP-50, temperature program: 11 minutes isothermal at 40° C., then heating at a rate of 10° C./min to 280° C., gas chromatography: Hewlett Packard HP 5890)

All examples were carried out under a protective gas atmosphere of argon. The advantageous specification of the starting materials BD, HCN, 3PN and 2M3BN can be taken from WO 03/045552.

The abbreviation nickel(0) (m/p-tolyl phosphite) represents a mixture containing 2.35% by weight of Ni(0), 19% by weight of 3-pentenenitrile and 78.65% by weight of m/p-tolyl phosphite having an m:p ratio of 2:1.

The chelate ligands used were:

Ligand 1

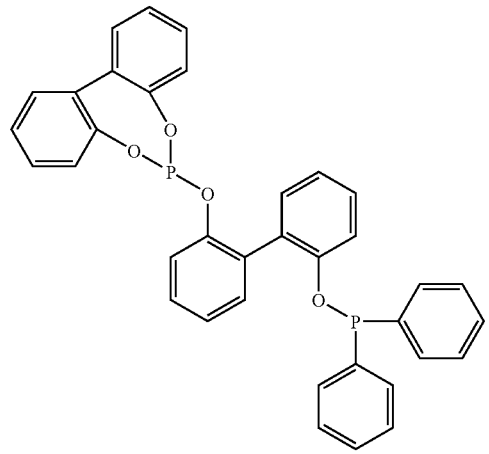

Ligand 2

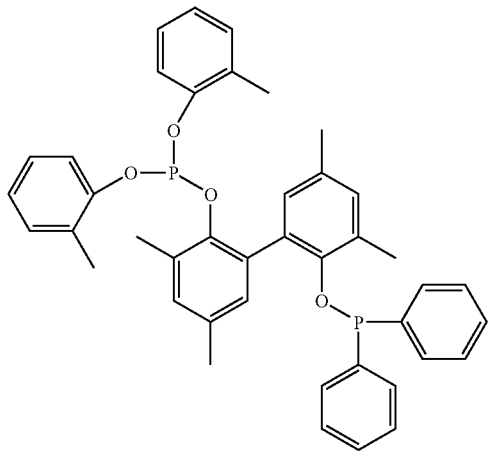

Ligand 3

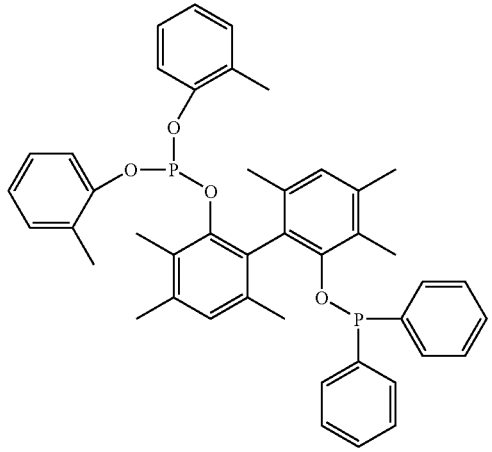

-continued

Ligand 4

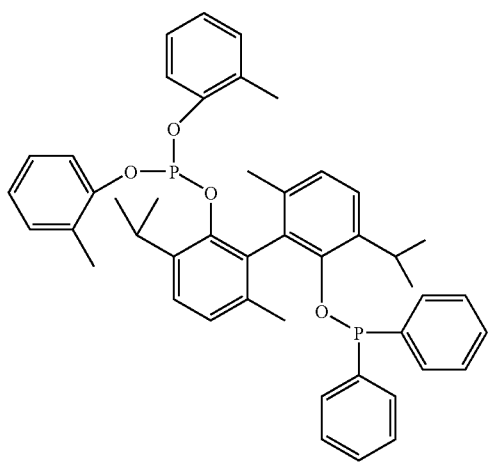

Ni(COD)$_2$ represents Ni(0)-bis-(1,4-cyclooctadiene), 2M3BN represents 2-methyl-3-butenenitrile, t2M2BN represents trans-2-methyl-2-butenenitrile, c2M2BN represents cis-2-methyl-2-butenenitrile, t2PN represents trans-2-pentenenitrile, 4PN represents 4-pentenenitrile, t3PN represents trans-3-pentenenitrile, c3PN represents cis-3-pentenenitrile, MGN represents methylglutaronitrile, 3PN represents the sum of t3PN and c3PN, BD represents 1,3-butadiene, HCN represents hydrocyanic acid, ADN represents adiponitrile, and THF represents tetrahydrofuran.

Example 1-3

Hydrocyanation of BD to 2M3BN/3PN with subsequent 2M3BN isomerization

Example 1 (Comparative)

(0.51 mmol of Ni(0))

Ligand 1

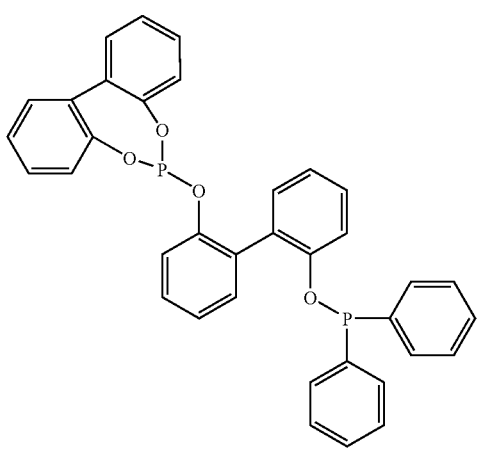

1 eq. of Ni(COD)$_2$ is stirred with 3 eq. of ligand 1 in THF for 20 min. This solution is admixed with 797 eq. of BD, charged into a glass autoclave at 25° C. and heated to 90° C. Over 60 min, 465 eq. of HCN in THF are now metered in and stirring is continued at 90° C. for a further 75 min. After 135 min, the 2M3BN/3PN ratio is determined by GC (GC area percent). The 2M3BN/3PN ratio was 1.9/1.

Subsequently, the entire mixture is heated to 115° C. for 60 min in order to directly isomerize 2M3BN to 3PN.

The HCN conversion to 2M3BN/3PN was >95% (GC area percent, internal standard: ethylbenzene). The 2M3BN/3PN ratio was 1.8/1.

Example 2 (Inventive)

(0.53 mmol of Ni(0))

Ligand 2

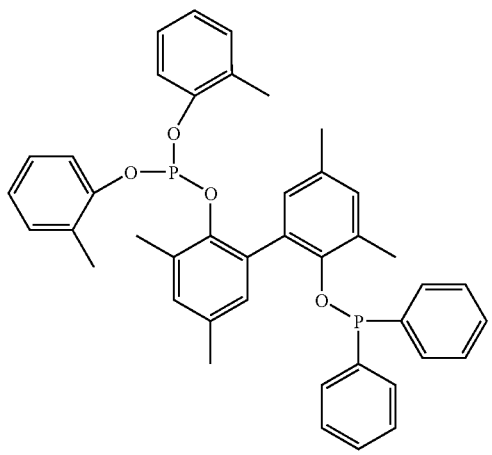

Ligand Synthesis:

In an argon atmosphere, 40 mmol of 2,2'-dihydroxy-3,3', 5,5'-tetramethylbiphenol and 160 mmol of triethylamine are initially charged at −15° C. in 120 ml of toluene in a 500 ml flask. At this temperature, 44 mmol of diphenylchlorophosphine dissolved in 40 ml of toluene are added dropwise within 40 min. The mixture is stirred at −15° C. for a further 6 h. At −15° C., 40 mmol of di-o-cresyl chlorophosphite dissolved in 40 ml of toluene are added dropwise to the mixture. The mixture is allowed to come to room temperature and stirred for a further 15 h. The mixture is filtered and the filtrate fully concentrated. 25.3 g of product are obtained. $^{31}$P NMR (C$_6$D$_6$): 133.5 ppm and 112.8 ppm; bisphosphinite impurities 112.5 ppm.

1 eq. of Ni(COD)$_2$ is stirred with 3 eq. of ligand 2 in THF for 20 min. This solution is admixed with 740 eq. of BD, charged into a glass autoclave at 25° C. and heated to 80° C. Over 100 min, 465 eq. of HCN in THF are now metered in and stirred at 80° C. for a further 20 min. After 120 min, the 2M3BN/3PN ratio is determined by gas GC (GC area percent). The 2M3BN/3PN ratio was 1.5/1.

Subsequently, the entire batch is heated to 115° C. for 60 min in order to isomerize 2M3BN directly to 3PN.

The HCN conversion to 2M3BN/3PN was >95% (GC area percent, internal standard: ethylbenzene). The 2M3BN/3PN ratio was 1/4.6.

Example 3 (Inventive)

(0.76 mmol of Ni(0))

Ligand 3

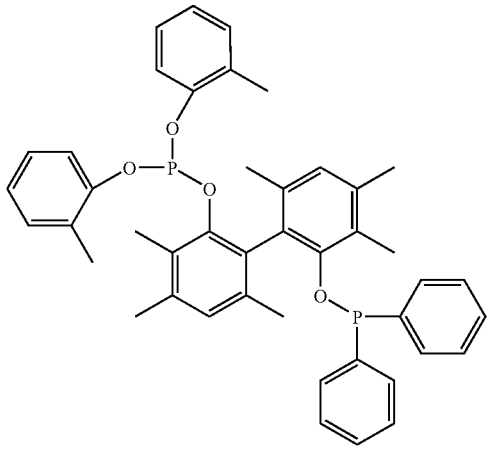

Ligand Synthesis:

In an argon atmosphere, 40 mmol of 2,2'-dihydroxy-3,3', 5,5',6,6'-hexamethylbiphenol and 160 mmol of triethylamine are initially charged at −15° C. in 120 ml of toluene in a 500 ml flask. At this temperature, 44 mmol of diphenylchlorophosphine dissolved in 40 ml of toluene are added dropwise within 40 min. The mixture is stirred at −15° C. for a further 6 h. At −15° C., 40 mmol of di-o-cresyl chlorophosphite dissolved in 40 ml of toluene are added dropwise to the mixture. The mixture is allowed to come to room temperature and stirred for a further 15 h. The mixture is filtered and the filtrate fully concentrated. 21.5 g of product are obtained. $^{31}$P NMR ($C_6D_6$): 134.7 ppm and 110.6 ppm.

1 eq. of Ni(COD)$_2$ is stirred with 3 eq. of ligand 3 in THF for 20 min. This solution is admixed with 770 eq. of BD, charged into a glass autoclave at 25° C. and heated to 80° C. Over 60 min, 465 eq. of HCN in THF are now metered in and stirred at 80° C. for a further 40 min. After 100 min, the 2M3BN/3PN ratio is determined by GC (GC area percent). The 2M3BN/3PN ratio was 2.5/1.

Subsequently, the entire batch is heated to 115° C. for 60 min in order to isomerize 2M3BN directly to 3PN.

The HCN conversion to 2M3BN/3PN was >95% (GC area percent, internal standard: ethylbenzene). The 2M3BN/3PN ratio was 1/2.6.

Example 4-8

Isomerization of 2M3BN to 3PN

Example 4 (Comparative)

(0.5 mmol of Ni(0))

1 eq. of nickel(0) (m4p-tolyl phosphite)$_{5-7}$ is admixed with 465 eq. of 2M3BN and heated to 115° C. After 90 min and after 180 min, GC samples are taken from the reaction mixture and analyzed by GC (GC area percent).

| Time | 2M3BN | t2M2BN | c2M2BN | t2PN | 4PN/t3PN/c3PN | 3PN/2M3BN |
|---|---|---|---|---|---|---|
| 90 min | 84.5 | 1.3 | 0.3 | 0 | 13.0 | 0.15 |
| 180 min | 72.4 | 1.5 | 0.5 | 0 | 24.4 | 0.34 |

Example 5 (Comparative)

(0.51 mmol of Ni(0))

1 eq. of Ni(COD)$_2$ is admixed with 3 eq. of ligand 1 and 465 eq. of 2M3BN, stirred at 25° C. for 1 h and heated to 115° C. After 0, 1 h and after 3 h, GC samples are taken from the reaction mixture and analyzed by GC (GC area percent).

| Time | 2M3BN | c,t-2M2BN | c,t-2PN | 4PN | c,t-3PN | 3PN/2M3BN |
|---|---|---|---|---|---|---|
| 0 h | 94.8 | 4.96 | 0 | 0 | 0 | 0 |
| 1 h | 86.04 | 5.98 | 0 | 0 | 6.85 | 0.08 |
| 3 h | 79.67 | 7.09 | 0 | 0 | 11.28 | 0.14 |

Example 6 (Inventive)

(0.4 mmol of Ni(0))

1 eq. of Ni(COD)$_2$ is admixed with 3 eq. of ligand 2 and 465 eq. of 2M3BN, stirred at 25° C. for 1 h and heated to 115° C. After 0, 5 min and after 25 min, GC samples are taken from the reaction mixture and analyzed by GC (GC area percent).

| Time | 2M3BN | 2M2BN | 2PN | 3PN + 4PN | 3PN/2M3BN |
|---|---|---|---|---|---|
| 0 min | 85.5 | 4.1 | 0 | 8.4 | 0.1 |
| 5 min | 51.4 | 4.1 | 0 | 42.3 | 1.2 |
| 25 min | 4.8 | 4.0 | 0 | 89.1 | 18.6 |

Example 7 (Inventive)

(0.38 mmol of Ni(0))

1 eq. of Ni(COD)$_2$ is admixed with 3 eq. of ligand 3 and 465 eq. of 2M3BN, stirred at 25° C. for 1 h and heated to 115° C. After 0, 5 min and after 25 min, GC samples are taken from the reaction mixture and analyzed by GC (GC area percent).

| Time | 2M3BN | 2M2BN | 2PN | 3PN + 4PN | 3PN/2M3BN |
|---|---|---|---|---|---|
| 0 min | 91.1 | 4.5 | 0 | 2.9 | 0.03 |
| 5 min | 68.1 | 4.4 | 0 | 25.3 | 0.38 |
| 25 min | 4.8 | 4.4 | 0.1 | 88.4 | 18.4 |

Example 8 (Inventive)

(0.35 mmol of Ni(0))

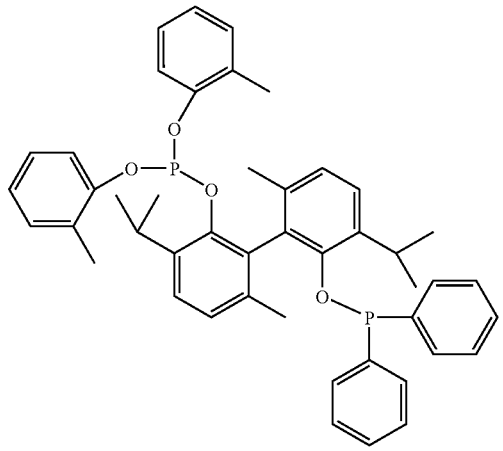

Ligand 4

Ligand Synthesis:

In an argon atmosphere, 40 mmol of 2,2'-dihydroxy-3,3'-diisopropyl-6,6'-dimethylbiphenol and 44 mmol of diphenylchlorophosphine are initially charged at −15° C. in 120 ml of toluene in a 500 ml flask. At this temperature, 160 mmol of triethylamine dissolved in 40 ml of toluene are added dropwise within 40 min. The mixture is stirred at −15° C. for a further 6 h. At −15° C., 40 mmol of di-o-cresyl chlorophosphite dissolved in 40 ml of toluene are added dropwise to the mixture. The mixture is allowed to come to room temperature and stirred for a further 15 h. The mixture is filtered and the filtrate fully concentrated. 21.5 g of product are obtained. $^{31}$P NMR ($C_6D_6$): 132.5 ppm and 113.5 ppm.

1 eq. of Ni(COD)$_2$ is admixed with 3 eq. of ligand 4 and 465 eq. of 2M3BN, stirred at 25° C. for 1 h and heated to 115° C. After 0, 5 min and after 25 min, GC samples are taken from the reaction mixture and analyzed by GC (GC area percent).

| Time | 2M3BN | 2M2BN | 2PN | 3PN + 4PN | 3PN/2M3BN |
|---|---|---|---|---|---|
| 0 min | 89.1 | 4.8 | 0 | 4.2 | 0.05 |
| 5 min | 78.8 | 4.6 | 0 | 14.9 | 0.19 |
| 25 min | 41.5 | 4.4 | 0 | 52.5 | 1.27 |

Example 9-13

Hydrocyanation of 3PN to ADN

Example 9 (Comparative)

(0.6 mmol of Ni(0))

1 eq. of nickel(0) (m-/p-tolyl phosphite)$_{5-7}$ is admixed with 365 eq. of 3PN, stirred at 25° C. for one hour and heated to 70° C. 1 eq. of ZnCl$_2$ is added to this mixture and it is stirred for a further 5 min. In an Ar carrier gas stream, 94 eq. of HCN/h*Ni are now injected. After 30 min, 60 min and 150 min, GC samples are taken from the reaction mixture and analyzed by GC (GC area percent, internal standard: ethylbenzene).

| Time | MGN | ADN | ADN selectivity (%) |
|---|---|---|---|
| 30 min | 3.35 | 10.75 | 76.2 |
| 60 min | 6.87 | 26.39 | 79.3 |
| 150 min | 7.11 | 27.82 | 79.6 |

Example 10 (Comparative)

(0.45 mmol of Ni(0))

1 eq. of Ni(COD)$_2$ is admixed with 3 eq. of ligand 1 and 365 eq. of 3PN, stirred at 25° C. for one hour and heated to 70° C. 1 eq. of ZnCl$_2$ is added to this mixture and it is stirred for a further 5 min. In an Ar carrier gas stream, 286 eq. of HCN/h*Ni are now injected. After 60 min, a GC sample is taken from the reaction mixture and analyzed by GC (GC area percent, internal standard: ethylbenzene).

| Time | MGN | ADN | ADN selectivity (%) |
|---|---|---|---|
| 60 min | 1.4 | 8.4 | 86.0 |

Example 11 (Inventive)

(0.37 mmol of Ni(0))

1 eq. of Ni(COD)$_2$ is admixed with 3 eq. of ligand 2 and 365 eq. of 3PN, stirred at 25° C. for one hour and heated to 40° C. 1 eq. of ZnCl$_2$ is added to this mixture and it is stirred for a further 5 min. In an Ar carrier gas stream, 309 eq. of HCN/h*Ni are now injected. After 88 min, a GC sample is taken from the reaction mixture and analyzed by GC (GC area percent, internal standard: ethylbenzene).

| Time | MGN | ADN | ADN selectivity (%) |
|---|---|---|---|
| 88 min | 6.5 | 68.3 | 91.3 |

Example 12 (Inventive)

(0.36 mmol of Ni(0))

1 eq. of Ni(COD)$_2$ is admixed with 3 eq. of ligand 3 and 365 eq. of 3PN, stirred at 25° C. for one hour and heated to 40° C. 1 eq. of ZnCl$_2$ is added to this mixture and it is stirred for a further 5 min. In an Ar carrier gas stream, 302 eq. of HCN/h*Ni are now injected. After 80 min, a GC sample is taken from the reaction mixture and analyzed by GC (GC area percent, internal standard: ethylbenzene).

| Time | MGN | ADN | ADN selectivity (%) |
|---|---|---|---|
| 80 min | 7.2 | 62.4 | 89.7 |

Example 13 (Inventive)

(0.39 mmol of Ni(0))

1 eq. of Ni(COD)₂ is admixed with 3 eq. of ligand 4 and 365 eq. of 3PN, stirred at 25° C. for one hour and heated to 40° C. 1 eq. of ZnCl₂ is added to this mixture and it is stirred for a further 5 min. In an Ar carrier gas stream, 289 eq. of HCN/h*Ni are now injected. After 82 min, a GC sample is taken from the reaction mixture and analyzed by GC (GC area percent, internal standard: ethylbenzene).

| Time | MGN | ADN | ADN selectivity (%) |
|---|---|---|---|
| 82 min | 5.4 | 59.2 | 91.7 |

We claim:

1. A phosphinite phosphite selected from the group consisting of Formula 1, Formula 2, Formula 3, Formula 4, Formula 5 and Formula 6,

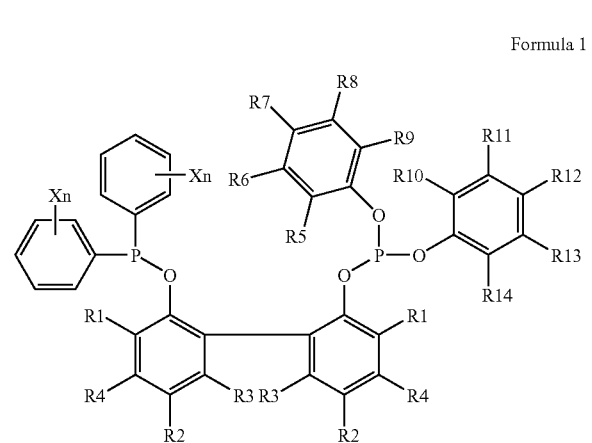

Formula 1

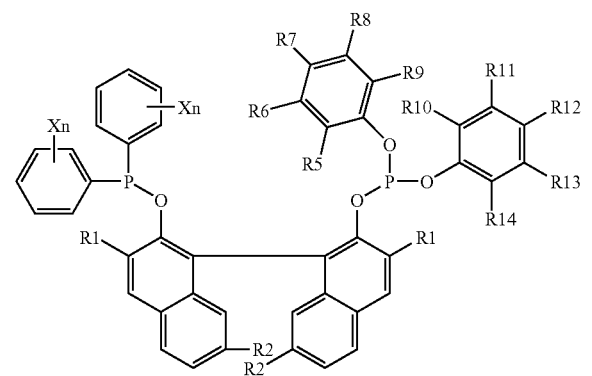

Formula 2

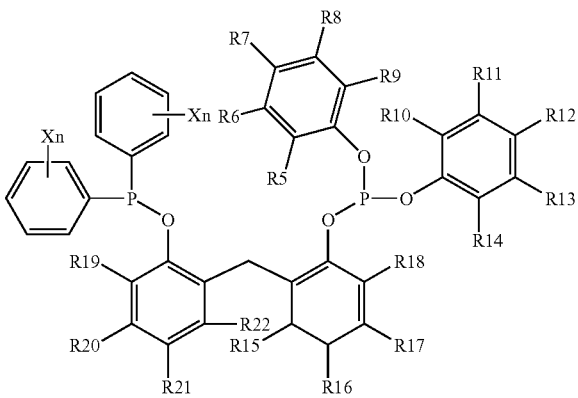

Formula 3

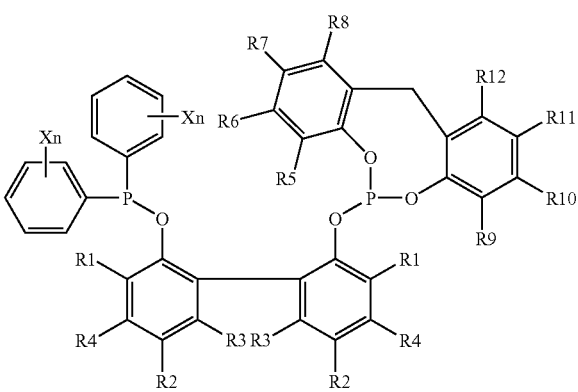

Formula 4

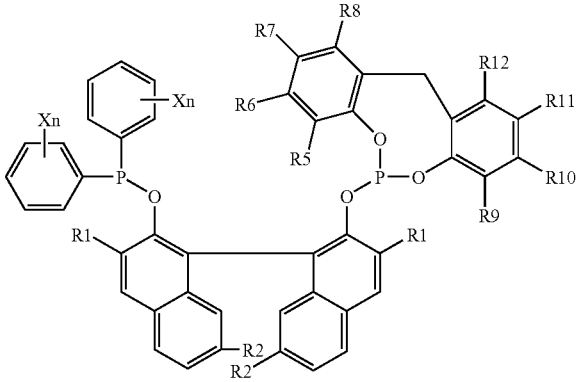

Formula 5

-continued

Formula 6

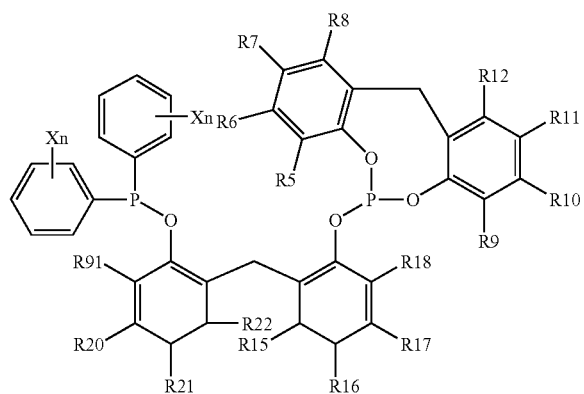

where
R1, R2, R4 are each independently an alkyl or alkylene group having from 1 to 8 carbon atoms, with the proviso that at least one of the R1, R2, R4 groups is not H,
R5 to R22 are each independently H, an alkyl or alkylene group having from 1 to 8 carbon atoms,
R3 is H, methyl or ethyl,
n is 0,1 or 2,
X is F, Cl or $CF_3$ if n is 1 or 2,
and mixtures thereof.

2. A phosphinite phosphite as claimed in claim 1 where R1, R2, R4, R5, R7, R8, R10, R12, R13 are each independently selected from the group consisting of H, methyl, ethyl, n-propyl, isopropyl and t-butyl.

3. A transition metal complex containing a phosphinite phosphite as claimed in claim 1 as a ligand.

4. A transition metal complex as claimed in claim 3, wherein the transition metal is nickel.

5. A process for preparing a transition metal complex as claimed in claim 3 comprising reacting a transition metal or a chemical compound containing a transition metal with a phosphinite phosphite as claimed in claim 1.

6. A catalyst comprising the transition metal complex as claimed in claim 3.

7. A method for the addition of hydrocyanic acid to an olefinic double bond comprising hydrocyanating an olefin using the catalyst as claimed in claim 6.

8. A method for the isomerization of organic nitriles comprising isomerizing an organic nitrile using the catalyst as claimed in claim 6.

9. A phosphinite phosphite of claim 1 wherein the phosphinite phosphite is of Formula 1.

10. A phosphinite phosphite of claim 1 wherein the phosphinite phosphite is of Formula 2.

11. A phosphinite phosphite of claim 1 wherein the phosphinite phosphite is of Formula 3.

12. A phosphinite phosphite of claim 1 wherein the phosphinite phosphite is of Formula 4.

13. A phosphinite phosphite of claim 1 wherein the phosphinite phosphite is of Formula 5.

14. A phosphinite phosphite of claim 1 wherein the phosphinite phosphite is of Formula 6.

15. A method of producing a transition metal complex comprising complex a transition metal with the phosphinite phosphite as claimed in claim 1.

* * * * *